(12) United States Patent
Miyake et al.

(10) Patent No.: US 10,954,174 B2
(45) Date of Patent: Mar. 23, 2021

(54) PROCESS FOR PREPARING (7Z)-7-TRICOSENE

(71) Applicant: Shin-Etsu Chemical Co., Ltd., Tokyo (JP)

(72) Inventors: Yuki Miyake, Niigata (JP); Takeshi Kinsho, Niigata (JP); Yusuke Nagae, Niigata (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 16/872,555

(22) Filed: May 12, 2020

(65) Prior Publication Data

US 2020/0361836 A1    Nov. 19, 2020

(30) Foreign Application Priority Data

May 16, 2019  (JP) .............................. JP2019-093001

(51) Int. Cl.
*C07C 2/60* (2006.01)
*C07C 11/02* (2006.01)

(52) U.S. Cl.
CPC ................ *C07C 2/60* (2013.01); *C07C 11/02* (2013.01)

(58) Field of Classification Search
CPC ....... C07C 2/60; C07C 11/02; C07C 2523/72; C07C 1/326
See application file for complete search history.

(56) References Cited

U.S. PATENT DOCUMENTS

| | | | | |
|---|---|---|---|---|
| 3,798,273 A * | 3/1974 | Cargill | ...................... | C07C 1/22 |
| | | | | 568/417 |
| 3,851,007 A * | 11/1974 | Eiter | ......................... | C07C 5/09 |
| | | | | 585/254 |
| 3,932,616 A * | 1/1976 | Meresz | ................... | C07C 11/02 |
| | | | | 585/16 |
| 3,948,803 A | 4/1976 | Carney | | |
| 4,016,220 A * | 4/1977 | Kupper | ..................... | C07C 6/04 |
| | | | | 585/643 |
| 4,749,818 A * | 6/1988 | Byers | ...................... | C07C 1/326 |
| | | | | 585/324 |
| 4,922,049 A * | 5/1990 | Byers | ...................... | C07C 1/326 |
| | | | | 585/327 |
| 5,481,040 A * | 1/1996 | Fukumoto | ................. | C07C 1/34 |
| | | | | 568/9 |
| 2012/0321588 A1 | 12/2012 | Fujii et al. | | |
| 2017/0335216 A1* | 11/2017 | Hommeltoft | ......... | C07C 45/455 |

FOREIGN PATENT DOCUMENTS

JP    2013177359    9/2013

OTHER PUBLICATIONS

Battu et al. "Synthesis of (Z)-7-heneicosene and (Z)-7tricosene via organoboranes—Part V" Indian Journal of Chemistry, 388:1104-1105 (1999).
Extended European Search Report corresponding to European Patent Application No. 20174081.8 (6 pages) (dated Oct. 13, 2020).
Gibb et al. "(Z)-7-Tricosene and Monounsaturated Ketones as Sex Pheromone Components of the Australian Guava Moth *Coscinoptycha improbana*: Identification, Field Trapping, and Phenology" Journal of Chemical Ecology, 32 (1):221-237 (2006).
Sabharwal et al. "Short Synthesis of (Z)-7-Heneicosene and (Z)-7-Tricosene" Journal of the Indian Chemical Society, 66:411-412 (1989).

* cited by examiner

*Primary Examiner* — Ali Z Fadhel
(74) *Attorney, Agent, or Firm* — Myers Bigel, P.A.

(57) ABSTRACT

The present invention provides a process for preparing (7Z)-7-tricosene of the following formula (3): the process comprising a step of subjecting a nucleophilic reagent, (8Z)-8-pentadecenyl compound of the following general formula (1), wherein $M^1$ represents Li, $MgZ^1$, $CuZ^1$ or $CuLiZ^1$, wherein $Z^1$ represents a halogen atom or an (8Z)-8-pentadecenyl group, to a coupling reaction with a 1-halooctane compound of the following general formula (2), wherein $X^1$ represents a halogen atom, to produce (7Z)-7-tricosene (3).

2 Claims, No Drawings

PROCESS FOR PREPARING (7Z)-7-TRICOSENE

TECHNICAL FIELD

The present invention relates to a process for preparing (7Z)-7-tricosene which is a sex pheromone of peach fruit moth (scientific name: *Carposina sasakii*), pest against fruits such as apples and peaches.

BACKGROUND ART

Peach fruit moth is a serious pest against Rosaeeae fruits such as apples and peaches. Larvae of peach fruit moth eat and penetrate into the fruits, so that a damage tolerance level is low. Insecticides do not easily reach the larvae which already penetrated into the fruits, which makes it difficult to control the larvae. At present, the national government is making efforts to increase export of Japanese foodstuffs, and the volume of the exported fruits such as apples and peaches is increasing. If larvae of the peach fruit moth are found in export inspection in Japan, the Taiwan authority, for instance, prohibits export from a packaging facility where such fruits were packaged. In addition, on a first occasion where larvae of the peach fruit moth are found in import inspection in Taiwan during an exportation period, export from the relevant prefecture is prohibited; and on a second occasion, export from all over Japan is prohibited. This provisional prohibition is not lifted until an improvement plan is submitted to the Taiwan authority and the authority approves it. As described above, it is necessary to almost completely control the peach fruit moth for exportation of fruits. Accordingly, communication disruption agents with sex pheromones is carried out for the control of the peach fruit moth in addition to the control by insecticides in the areas of peach production, such as Fukushima Prefecture, Yamanashi Prefecture and Okayama Prefecture.

It has been revealed that the sex pheromone of the peach fruit moth is a mixture of (13Z)-13-eicosen-10-one and (7Z)-7-tricosene in a weight ratio of 19:81 (Patent Literature 1, mentioned below). Processes for producing (7Z)-7-tricosene have been reported, such as, for example, a synthesis by a coupling reaction between (7Z)-7-tridecenylmagnesium chloride and 1-bromodecane (Patent Literature 1), a synthesis by a coupling reaction between (4Z)-4-undecenylmagnesium bromide and 1-bromododecane (Non-Patent Literature 1, mentioned below), a synthesis by a coupling reaction between 1-octyn-1-yllithium and 1-bromopentadecane, followed by catalytic reduction using a palladium catalyst (Non-Patent Literature 2, mentioned below).

LIST OF THE PRIOR ART

Patent Literature

[Patent Literature 1] Japanese Patent Application Laid-Open No. 2013-177359

Non-Patent Literatures

[Non-Patent Literature 1] A. R. Gibb et al., J. Chem. Ecol., 2006, 32(1), 221-237.

[Non-Patent Literature 2] S. Arun et al., S. Indian. Chem., 1989, 66, 411-412.

SUMMARY OF THE INVENTION

Some improvement is required in the purification of (7Z)-7-tricosene in the synthetic processes in Patent Literature 1 and Non-Patent Literature 1. A homo-coupling product of a nucleophilic reagent with an alkyl halide compound is by-produced in the coupling reaction. Since the nucleophilic reagent having 13 carbon atoms and the alkyl halide compound having 10 carbon atoms were used in Patent Literature 1, (7Z,19Z)-7,19-hexacosadiene having 26 carbon atoms and eicosane having 20 carbon atoms were by-produced. Since the nucleophilic reagent having 11 carbon atoms and the alkyl halide compound having 12 carbon atoms were used in Non-Patent Literature 1, (7Z,15Z)-7,15-docosadiene having 22 carbon atoms and tetracosane having 24 carbon atoms were by-produced. These hydrocarbon compounds having 20 to 26 carbon atoms have boiling points very close to that of the target chemical compound, (7Z)-7-tricosene having 23 carbon atoms, so that an industrial separation by distillation of them is difficult. Accordingly, non-industrial methods such as separation by column chromatography are inevitably employed. In Non-Patent Literature 2, the yield of the coupling reaction is 38%, and the yield of the catalytic reduction is 35% and, thus, the yield in these two steps is 13%, Which is extremely low.

The present invention has been made in these circumstances, and aims it to provide an efficient and economical processes for preparing (7Z)-7-tricosene.

As a result of the intensive researches to overcome the aforesaid problems of the prior art, the present inventors have found that (7Z)-7-tricosene is prepared efficiently and economically by a coupling reaction between a nucleophilic reagent, (8Z)-8-pentadecenyl compound, which can be conveniently prepared from a (7Z)-15-halo-7-pentadecene compound which can be synthesized in a large amount at low costs, with a 1-halooctane compound which is industrially available at low costs, and thus have completed the present invention.

According to one aspect of the present invention, there is provided a process for preparing (7Z)-7-tricosene of the following formula (3):

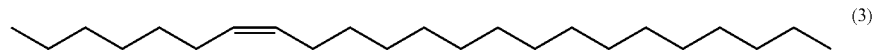 [SMILES: CCCCCC/C=C\CCCCCCCCCCCCCCC]

the process comprising a step of subjecting a nucleophilic reagent, (8Z)-8-pentadecenyl compound of the following general formula (1):

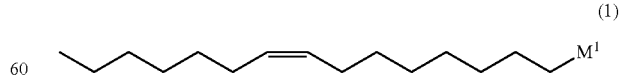

wherein $M^1$ represents Li, $MgZ^1$, $CuZ^1$ or $CuLiZ^1$, wherein $Z^1$ represents a halogen atom or an (8Z)-8-pentadecenyl group, to a coupling reaction with a 1-halooctane compound of the following general formula (2):

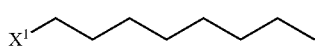

(2)

wherein $X^1$ represents a halogen atom,
to produce (7Z)-7-tricosene (3).

An embodiment of the present invention makes it possible to economically and efficiently prepare (7Z)-7-tricosene (3).

By-produced impurities are hexadecane having 16 carbon atoms and (7Z,23Z)-triacontadiene having 30 carbon atoms. The boiling points of these are much different from that of the target chemical compound, (7Z)-7-tricosene having 23 carbon atoms. Accordingly, the target chemical compound can be easily separated from the aforesaid impurities by distillation, whereby highly pure (7Z)-7-tricosene (3) can be produced.

DETAILED DESCRIPTION OF THE INVENTION

First, a (7Z)-15-halo-7-pentadecene compound of the following general formula (6), which is used as a raw material in the preparation of a nucleophilic reagent, (8Z)-8-pentadecenyl compound (1), will be described hereinafter.

$X^4$ in the (7Z)-15-halo-7-pentadecene compound (6) represents a halogen atom. Examples of the halogen atom, $Z^2$, include a chlorine atom, a bromine atom, and an iodine atom.

The (7Z)-15-halo-7-pentadecene compound (6) can be synthesized, for example, by a step of subjecting a nucleophilic reagent, (3Z)-3-decenyl compound of the following general formula (4), with a 1-halo-5-halopentane compound of the following general formula (5) to produce (7Z)-15-halo-7-pentadecene compound (6).

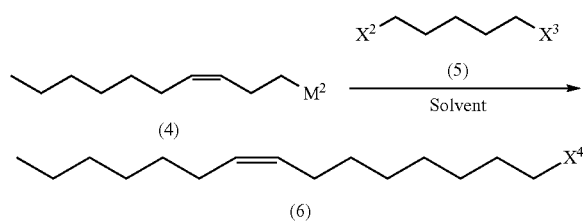

$M^2$ in the nucleophilic reagent, (3Z)-3-decenyl compound (4), represents Li, $MgZ^2$, $CuZ^2$ or $CuLiZ^2$, wherein $Z^2$ represents a halogen atom or a (3Z)-3-decenyl group. Examples of the halogen atom, $Z^2$, include a chlorine atom, a bromine atom, and an iodine atom.

Examples of the nucleophilic reagent, (3Z)-3-decenyl compound (4), include (3Z)-3-decenyl lithium; a (3Z)-3-decenylmagnesium halide reagent (Grignard reagent) such as (3Z)-3-decenylmagnesium chloride, (3Z)-3-decenylmagnesium bromide and (3Z)-3-decenylmagnesium iodide; and a Gilman reagent such as lithium bis[(3Z)-3-decenyl]cuprate, with the (3Z)-3-decenylmagnesium halide reagent being preferred, in view of the versatility.

The nucleophilic reagent, (3Z)-3-decenyl compound (4), may be used either alone or in combination thereof. The nucleophilic reagent, (3Z)-3-decenyl compound (4), may be commercially available one or may be synthesized in house.

The nucleophilic reagent, (3Z)-3-decenyl compound (4), can be prepared from a (3Z)-1-halo-3-decene compound (7), as will be explained below.

The nucleophilic reagent, (3Z)-3-decenyl compound (4), can be prepared in a manner known per se in the art.

For instance, the (3Z)-3-decenylmagnesium halide reagent (4: $M^2=MgX^5$) as the nucleophilic reagent, (3Z)-3-decenyl compound (4), can be produced by a step of reacting a (3Z)-1-halo-3-decene compound of the following general formula (7) with magnesium in a solvent to produce the (3Z)-3-decenylmagnesium halide reagent (4: $M^2=MgX^5$).

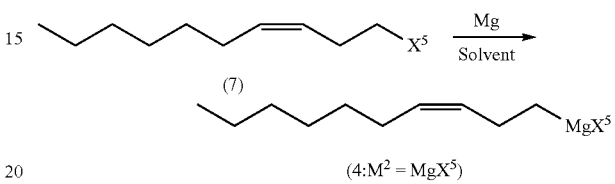

$X^5$ represents a halogen atom. Examples of the halogen atom $X^5$ include a chlorine atom, a bromine atom, and an iodine atom.

Examples of the (3Z)-1-halo-3-decene compound (7) include (3Z)-1-chloro-3-decene, (3Z)-1-bromo-3-decene, and (3Z)-1-iodo-3-decene.

The (3Z)-1-halo-3-decene compound (7) may be used either alone or in combination thereof. The (3Z)-1-halo-3-decene compound (7) may be commercially available one or may be synthesized in house.

An amount of magnesium to be used is preferably from 1.0 to 2.0 gram atoms per mol of the (3Z)-1-halo-3-decene compound (7) in view of the completion of the reaction.

Examples of the solvent include ether solvents such as tetrahydrofuran, diethyl ether and 4-methyltetrahydropyran; and hydrocarbon solvents such as toluene, xylene, and hexane. Tetrahydrofuran is preferred in view of a reaction rate in the formation of the Grignard reagent.

An amount of the solvent is preferably from 100 to 1000 g per mol of the (3Z)-1-halo-3-decene compound (7) in view of the reactivity.

A reaction temperature varies, depending on a solvent used, and is preferably from 30 to 120° C. in view of the reactivity.

A reaction time varies, depending on a solvent used or a production scale, and is preferably from 1 to 30 hours in view of the reactivity.

An amount of the nucleophilic reagent, (3Z)-3-decenyl compound (4), to be used is preferably from 0.8 to 1.4 mol per mol of the 1-halo-5-halopentane compound (5) in view of the economy.

$X^2$ and $X^3$ in the 1-halo-5-halopentane compound (5) may be same with or different from each other and represent a halogen atom. Examples of the halogen atom, $X^2$ and $X^3$, include a chlorine atom, a bromine atom, and an iodine atom.

Examples of a combination of $X^2$ with $X^3$ include a chlorine atom with a chlorine atom, a bromine atom with a chlorine atom, a chlorine atom with an iodine atom, a bromine atom with a bromine atom, a bromine atom with an iodine atom, and an iodine atom with an iodine atom.

Examples of the 1-halo-5-halopentane compound (5) include 1,5-dichloropentane, 1-bromo-5-chloropentane, 1-chloro-5-iodopentane, 1,5-dibromopentane, 1-bromo-5-iodopentane, and 1,5-diiodopentane.

The 1-halo-5-halopentane compound (5) may be used either alone or in combination thereof. The 1-halo-5-halopentane compound (5) may be commercially available one or may be synthesized in house.

In a case where $X^2$ and $X^3$ differ from each other, the coupling reaction may proceed with preference of a halogen atom having a higher reactivity, by appropriately selecting a catalyst or a reaction temperature, as will be explained below. For instance, when the 1-halo-5-halopentane compound (5) has a combinations of $X^2$ and $X^3$ which differ from each other, i.e., a chlorine atom with a bromine atom or a chlorine atom with an iodine atom, the (7Z)-15-halo-7-pentadecene compound (6) will have $X^4$ being a chlorine atom. Further, when the 1-halo-5-halopentane compound (5) has a combination of $X^2$ and $X^3$ is a bromine atom with an iodine atom, the (7Z)-15-halo-7-pentadecene compound (6) will have $X^4$ being a bromine atom.

A solvent may be used in the coupling reaction, if necessary. Examples of the solvent include hydrocarbon solvents such as toluene, xylene and hexane; ether solvents such as tetrahydrofuran, 4-methyltetrahydropyran, and diethyl ether; and polar solvents such as N,N-dimethylformamide, N,N-dimethylacetamide, N-methylpyrrolidone, dimethyl sulfoxide, γ-butyrolactone and acetonitrile. Toluene, tetrahydrofuran, 4-methyltetrahydropyran and acetonitrile are preferred, with tetrahydrofuran being more preferred, in view of the reactivity.

The solvent may be used either alone or in combination thereof. The solvent may be commercially available one.

An amount of the solvent is preferably from 30 to 2000 g per mol of the 1-halo-5-halopentane compound (5) in view of the reactivity.

A catalyst may be used in the coupling reaction, if necessary; in view of the reactivity. Examples of the catalyst include cuprous halides such as copper (I) chloride, copper (I) bromide, and copper (I) iodide; and cupric halides such as copper (II) chloride, capper (II) bromide, and copper (II) iodide, with cuprous halides being preferred, and with cuprous iodide being more preferred, in view of the reactivity.

The catalysts may be used either alone or in combination thereof. The catalyst may be commercially available one.

An amount of the catalyst is preferably from 0.003 to 0.300 mol per mol of the 1-halo-5-halopentane compound (5) in view of a reaction rate and easy post-processing.

When the catalyst is used, a cocatalyst may be used, if necessary. Examples of the cocatalyst include trialkyl phosphite compounds having 3 to 9 carbon atoms, such as triethyl phosphite; and phosphorus compounds, such as triarylphosphine compounds having 18 to 21 carbon atoms, such as triphenylphosphine, with triethyl phosphite being preferred, in view of the reactivity.

The cocatalyst may be used either alone or in combination thereof. The cocatalyst may be commercially available one.

An amount of the cocatalyst is preferably from 0.001 to 0.500 mol, more preferably from 0.001 to 0.050 mol, per mol of the 1-halo-5-halopentane compound (5).

In a case where the catalyst is used in the coupling reaction, lithium halide may be added, if necessary. Examples of the lithium halide include lithium chloride, lithium bromide and lithium iodide, with lithium chloride being preferred, in view of the reactivity.

An amount of the lithium halide is preferably front 0.005 to 0.250 mol per mol of the 1-halo-5-halopentane compound (5) in view of the reactivity.

A reaction temperature varies, depending on the nucleophilic reagent, (3Z)-3-decenyl compound (4) used, and is preferably from −78 to 70° C., more preferably −20 to 25° C., in view of the reactivity.

A reaction time varies, depending on a solvent used or a production scale, and is preferably from 3 to 45 hours in view of the reactivity.

Examples of the (7Z)-15-halo-7-pentadecene compound (6) include (7Z)-15-chloro-7-pentadecene, (7Z)-15-bromo-7-pentadecene, and (7Z)-15-iodo-7-pentadecene.

Next, a process for preparing (7Z)-7-tricosene (3) according to the following chemical reaction formula will be explained hereinafter. The process comprises a step of subjecting the aforesaid nucleophilic reagent, (8Z)-8-pentadecenyl compound (1), to a coupling reaction with the aforesaid 1-halooctane compound (2) to produce (7Z)-7-tricosene (3).

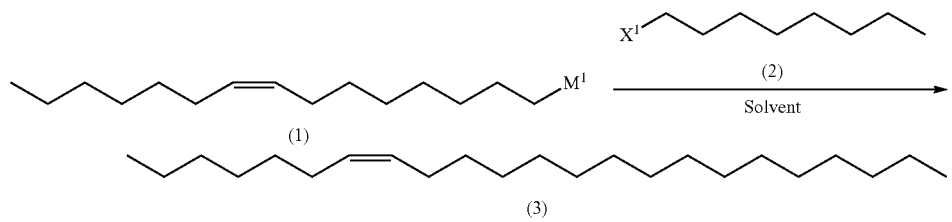

$M^1$ in the nucleophilic reagent, (8Z)-8-pentadecenyl compound (1), represents Li, $MgZ^1$, $CuZ^1$ or $CuLiZ^1$, wherein $Z^1$ represents a halogen atom or an (8Z)-8-pentadecenyl group. Examples of the halogen atom, $Z^1$, include a chlorine atom, a bromine atom, and an iodine atom.

Examples of the nucleophilic reagent, (8Z)-8-pentadecenyl compound (1), include (8Z)-8-pentadecenyl lithium; an (8Z)-8-pentadecenylmagnesium halide reagent (Grignard reagent) such as (8Z)-8-pentadecenylmagnesium chloride, (8Z)-8-pentadecenylmagnesium bromide and (87)-8-pentadecenylmagnesium iodide; and a Gilman reagent such as lithium bis[(8Z)-8-pentadecenyl]cuprate, with the (8Z)-8-pentadecenylmagnesium halide reagent being preferred, in view of the versatility.

The nucleophilic reagent, (8Z)-8-pentadecenyl compound (1), may be used either alone or in combination thereof. The nucleophilic reagent, (8Z)-8-pentadecenyl compound (1), may be commercially available one or may be synthesized in house.

The nucleophilic reagent, (8Z)-8-pentadecenyl compound, (1) may be prepared from the (7Z)-15-halo-7-pentadecene compound (6).

The nucleophilic reagent, (8Z)-8-pentadecenyl compound (1) may be prepared in a manner known per se in the art.

For instance, the (8Z)-8-pentadecenylmagnesium halide reagent (1: $M^1=MgX^4$) may be produced by reacting the aforesaid (7Z)-15-halo-7-pentadecene compound (6) with magnesium in a solvent to produce the (8Z)-8-pentadecenylmagnesium halide reagent (1: M¹=MgX⁴).

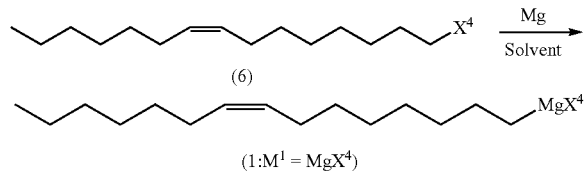

The (7Z)-15-halo-7-pentadecene compound (6) may be used either alone or in combination thereof. The (7Z)-15-halo-7-pentadecene compound (6) may be commercially available one or may be synthesized in house.

An amount of magnesium to be used is preferably from 1.0 to 2.0 grain atoms per mol of the (7Z)-15-halo-7-pentadecene compound (6) in view of the completion of the reaction.

Examples of the solvent include ether solvents such as tetrahydrofuran, diethyl ether and 4-methyltetrahydropyran, and hydrocarbon solvents such as toluene, xylene, and hexane. Tetrahydrofuran is preferred in view of a reaction rate in the formation of the Grignard reagent.

An amount of the solvent is preferably from 100 to 1000 g per mol of the (7Z)-15-halo-7-pentadecene compound (6) in view of the reactivity.

A reaction temperature varies, depending on a solvent used, and is preferably from 30 to 120° C. in view of the reactivity.

A reaction time varies, depending on a solvent used or a production scale, and is preferably from 1 to 30 hours in view of the reactivity.

An amount of the nucleophilic reagent, (8Z)-8-pentadecenyl compound (1) to be used, in the aforesaid coupling reaction is preferably from 0.8 to 1.2 mol per mol of the 1-halooctane compound (2) in view of the economy.

$X^1$ in the 1-halooctane compound (2) represent a halogen atom. Examples of the halogen atom, $X^1$, include a chlorine atom, a bromine atom, and an iodine atom.

Examples of the 1-halooctane compound (2) include 1-chlorooctane, 1-bromooctane, and 1-iodooctane.

The 1-halooctane compound (2) may be used either alone or in combination thereof. The 1-halooctane compound (2) may be commercially available one or may be synthesized in house.

A catalyst may be used in the coupling reaction, if necessary. Examples of the catalyst include cuprous halides such as copper (I) chloride, copper (I) bromide, and copper (I) iodide; and cupric halides such as copper (II) chloride, copper (II) bromide, and copper (II) iodide, with cuprous halides being preferred, and with copper (I) chloride being more preferred, in view of the reactivity.

An amount of the catalyst is preferably from 0.003 to 0.300 mol per mol of the 1-halooctane compound (2) in view of a reaction rate and easy post-processing.

When the catalyst is used, a cocatalyst may be used, if necessary. Examples of the cocatalyst include trialkyl phosphite compounds having 3 to 9 carbon atoms, such as triethyl phosphite; and phosphorus compounds, such as triarylphosphine compounds having 18 to 21 carbon atoms, such as triphenylphosphine, with triethyl phosphite being preferred, in view of the reactivity.

An amount of the cocatalyst is preferably from 0.001 to 0.500 mol, more preferably from 0.001 to 0.200 mol, per mol of the 1-halooctane compound (2).

In a case where the catalyst is used, lithium halide may be added, if necessary Examples of the lithium halide include lithium chloride, lithium bromide and lithium iodide, with lithium chloride being preferred, in view of the reactivity.

An amount of the lithium halide is preferably fruit 0.005 to 0.250 mol per mol of the 1-halooctane compound (2) in view of the reactivity.

A solvent may be used in the coupling reaction, if necessary. Examples of the solvent include hydrocarbon solvents such as toluene, xylene and hexane; ether solvents such as tetrahydrofuran, 4-methyltetrahydropyran, and diethyl ether; and polar solvents such as N,N-dimethylformamide, N,N-dimethylacetamide, N-methylpyrrolidone, dimethyl sulfoxide, γ-butyrolactone and acetonitrile. Toluene, tetrahydrofuran, 4-methyltetrahydropyran and acetonitrile are preferred, with tetrahydrofuran being more preferred, in view of the reactivity.

The solvent may be used either alone or in combination thereof. The solvent may be commercially available one.

An amount of the solvent is preferably from 30 to 2000 g per mol of the 1-halooctane compound (2) in view of the reactivity.

A reaction temperature varies, depending on the nucleophilic reagent used, (8Z)-8-pentadecenyl compound (1), and is preferably from −78 to 70° C., more preferably −20 to 25° C., in view of the reactivity.

A reaction time varies, depending on a solvent used or a production scale, and is preferably from 1 to 45 hours in view of the reactivity.

Hexadecane having 16 carbon atoms and (7Z,23Z)-triacontadiene having 30 carbon atoms are by-produced in the coupling reaction. The boiling points of these are much different from that of the target chemical compound, (7Z)-7-tricosene having 23 carbon atoms, Accordingly, the target chemical compound can be easily separated from the aforesaid impurities by distillation, whereby highly pure (7Z)-7-tricosene (3) can be produced.

EXAMPLE

The present invention will be further described with reference to the following Examples. It should be understood that the present invention is not limited to or by the Examples.

The term "purity" as used herein means an area percentage obtained by gas chromatography (GC), unless otherwise specified. The term "production ratio" means a ratio of area percentages obtained by GC. The term "yield" is calculated from the area percentages obtained by GC.

In the Examples, monitoring of the reactions and calculation of the yields were carried out in the following GC conditions.

<GC conditions> GC: Capillary gas chromatograph GC-2014, ex Shimadzu Corporation; column: DB-5, 0.25 mm×0.25 mmϕ×30 m; carrier gas: He (1.55 mL/min), detector: FID; column temperature: 150° C., elevated by 5° C./min, up to 230° C.

The yield was calculated by the following equation in consideration of putties (% GC) of a starting material and a product.

Yield (%)={[(weight of a product obtained by a reaction×% GC)/molecular weight of a product]÷[(weight of a starting material in a reaction×% GC)/molecular weight of a starting material]}×100

Example 1

(A) Preparation of (7Z)-15-chloro-7-pentadecene (6: $X^4$=Cl) which is the Raw Material for a Nucleophilic Reagent, (8Z)-8-pentadecenyl Compound (1)

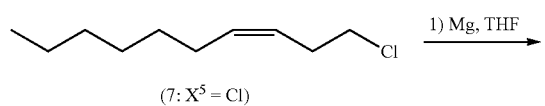

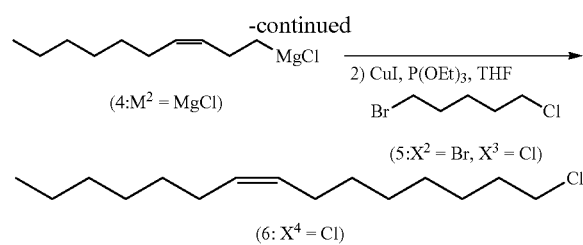

Magnesium (114.82 g, 4.73 gram atoms) and tetrahydrofuran (THF) (1350 g) were placed in a reactor and stirred at from 60 to 65° C. for 19 minutes. Then, (3Z)-1-chloro-3-decene (7: $X^5$=Cl) (786.20 g, 4.50 mol) was added dropwise to the reactor at from 60 to 75° C. After the completion of the dropwise addition, the reaction mixture was stirred at from 75 to 80° C. for 2 hours to form (3Z)-3-decenylmagnesium chloride (4: $M^2$=MgCl).

Next, cuprous iodide (8.57 g, 0.045 mop, triethyl phosphite (17.95 g, 0.11 mol), tetrahydrofuran (450 g) and 1-bromo-5-chloropentane (5: $X^2$=Br, $X^3$=Cl) (776.28 g, 4.19 mol) were placed in another reactor. Then, (3Z)-3-decenylmagnesium chloride (4: $M^2$=MgCl) obtained above was added dropwise at from −5 to 15° C. After the completion of the dropwise addition, stirring was continued at from 5 to 15° C. for 3.5 hours. Then, a mixture of ammonium chloride (45.90 g) and water (1212.26 g), and an aqueous 20% by weight hydrochloric acid (53.06 g) were added to the reaction mixture, followed by phase separation and removal of the aqueous phase. Then, the organic phase was concentrated at a reduced pressure and the residue was subjected to distillation at a reduced pressure to obtain (7Z)-15-chloro-7-pentadecene (6: $X^4$=Cl) (947.47 g, 3.80 mol, purity: 98.12%) in a yield of 90.62%.

The following are spectrum data of (7Z)-15-chloro-7-pentadecene (6: $X^4$=Cl) thus produced.

[Nuclear magnetic resonance spectrum] $^1$H-NMR (500 MHz CDCl$_3$): δ=0.89 (3H, t, J 7.1 Hz), 1.22-1.38 (14H, m), 1.38-1.47 (2H, m), 1.77 (2H, tt, J=6.9 Hz, 6.9 Hz), 1.94-2.07 (4H, m), 3.53 (2H, t, J=6.7 Hz), 5.30-5.40 (2H, m); $^{13}$C-NMR (500 MHz, CDCl$_3$): δ=14.09, 22.65, 26.84, 27.11, 27.21, 28.76, 28.97, 29.07, 29.60, 29.72, 31.77, 32.62, 45.12, 129.66, 130.04

[Mass spectrum] EI-Mass spectrum (70 eV): m/z 244 (M$^+$), 111, 97, 83, 69, 55, 41, 29

[Infrared absorption spectrum] (NaCl): ν=2954, 2926, 2855, 1465, 1310, 726, 655

(B) Preparation of (7Z)-7-tricosene (3) from (7Z)-15-chloro-7-pentadecene (6: $X^4$=Cl) which was Obtained in the Aforesaid Paragraph, (A)

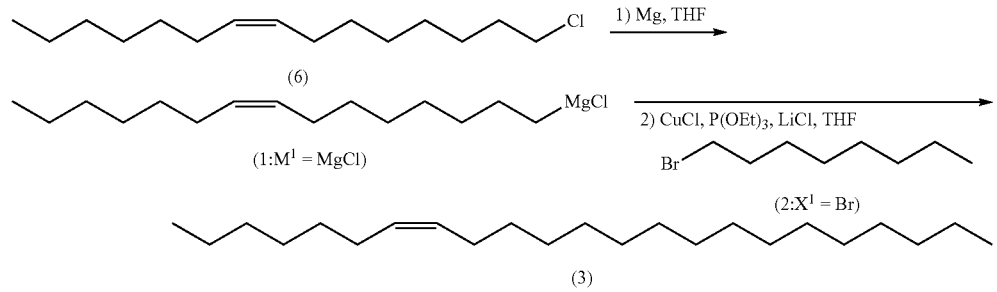

Magnesium (102.06 g, 4.20 gram atoms) and tetrahydrofuran (1200 g) were placed in a reactor at room temperature and stirred at from 60 to 65° C. for 30 minutes. Then, (7Z)-15-chloro-7-pentadecene (6: $X^4$=Cl) (998.12 g, 4.00 mol, purity: 98.12%) was added dropwise to the mixture at from 60 to 75° C. After the completion of the dropwise addition, the reaction mixture was stirred at from 75 to 80° C. for 2 hours to form (8Z)-8-pentadecenylmagnesium chloride (1: $M^1$=MgCl)

Next, cuprous chloride (4.47 g, 0.045 mol), triethyl phosphite (44.86 g, 0.27 mol), lithium chloride (3.10 g, 0.073 mol), tetrahydrofuran (400 g) and 1-bromooctane (2: $X^1$=Br) (772.48 g, 4.00 mol) were placed in another reactor. Then, (8Z)-8-pentadecenylmagnesium chloride (1: $M^1$=MgCl) obtained above was added dropwise at from −5 to 10° C. After the completion of the dropwise addition, stirring was continued at from 0 to 10° C. for 3 hours. Then, a mixture of ammonium chloride (42.11 g) and water (1088.42 g), and an aqueous 20% by weight hydrochloric acid (80.11 g) were added to the reaction mixture, followed by phase separation and removal of the aqueous phase. A mixture of sodium bicarbonate (50.00 g) and water (500.00 g) was added to the obtained organic layer, followed by phase separation. The organic phase was washed.

Next, the washed organic phase was concentrated at a reduced pressure and the residue was subjected to distillation at a reduced pressure to obtain (7Z)-7-tricosene (3) (1171.24 g, 3.59 mol, purity: 98.94%) in a yield of 89.8%. (7Z)-7-tricosene (3) thus obtained contained 0.45% GC of hexadecane having 16 carbon atoms, but (7Z, 23Z)-triacontadiene having 30 carbon atoms was not detected by GC.

The residue obtained in the concentration at a reduced pressure (but before the distillation) was analyzed by gas chromatography to confirmed that the residue contained 90.70% GC of the target (7Z)-7-tricosene (3), 0.76% GC of hexadecane as described above, and 1.37% GC of (7Z, 23Z)-triacontadiene as described above. This crude product was distilled at a reduced pressure. Hexadecane having 16 carbon atoms was first distilled off, and then (7Z)-7-tricosene (3) having 23 carbon atoms was distilled off in the middle stage of the distillation at a reduced pressure. As a result, highly pure (7Z)-7-tricosene (3) was produced. Since (7Z,23Z)-triacontadiene having 30 carbon atoms have a high boiling point, most of them remained in the distillation still after the distillation.

The following are spectrum data of the (7Z)-7-tricosene (3) thus produced.

[Nuclear magnetic resonance spectrum] $^1$H-NMR (500 MHz, CDCl$_3$): δ=0.88 (3H, t, J=7.3 Hz), 0.89 (3H, t, J=7.3 Hz), 1.22-1.37 (34H, m), 2.02 (4H, dt, J=6.3 Hz), 5.35 (2H, t-like, 4.2 Hz); $^{13}$C-NMR (500 MHz, CDCl$_3$): δ 14.10, 14.12, 22.67, 22.71, 27.21, 27.23, 29.00, 29.33, 29.38, 29.58, 29.67, 29.72, 29.76, 29.79, 31.80, 31.94, 129.90

[Mass spectrum] EI-Mass spectrum. (70 eV): m/z 322 (M$^+$), 153, 139, 125, 111, 97, 83, 69, 55, 43, 27

[Infrared absorption spectrum] (NaCl): ν=2956, 2923, 2853, 1466, 1378, 721

The invention claimed is:

1. A process for preparing (7Z)-7-tricosene of the following formula (3):

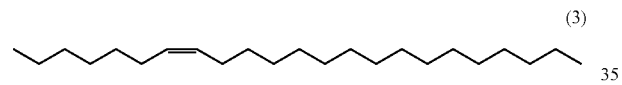

(3)

the process comprising a step of:
subjecting a nucleophilic reagent, (8Z)-8-pentadecenyl compound of the following general formula (1):

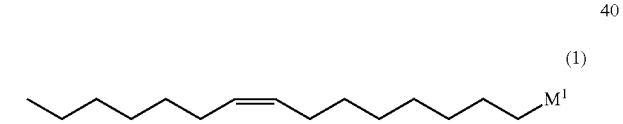

(1)

wherein M$^1$ represents Li, MgZ$^1$, CuZ$^1$ or CuLiZ$^1$, wherein Z$^1$ represents a halogen atom or an (8Z)-8-pentadecenyl group,
to a coupling reaction with a 1-halooctane compound of the following general formula (2):

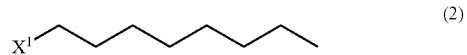

(2)

wherein X$^1$ represents a halogen atom,
to produce (7Z)-7-tricosene (3).

2. The process according to claim 1, further comprising:
subjecting a nucleophilic reagent, (3Z)-3-decenyl compound of the following general formula (4):

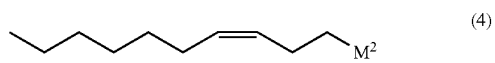

(4)

wherein M$^2$ represents Li, MgZ$^2$, CuZ$^2$ or CuLiZ$^2$, wherein Z$^2$ represents a halogen atom or a (3Z)-3-decenyl group,
to a coupling reaction with a 1-halo-5-halopentane compound of the following general formula (5):

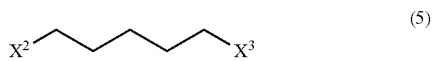

(5)

wherein X$^2$ and X$^3$ may be same with or different from each other and represent a halogen atom,
to produce (7Z)-15-halo-7-pentadecene compound of the following general formula (6):

(6)

wherein X$^4$ represents a halogen atom; and
producing the nucleophilic reagent, (8Z)-8-pentadecenyl compound (1), from the (7Z)-15-halo-7-pentadecene compound (6).

* * * * *